United States Patent
Truschel et al.

(10) Patent No.: US 10,576,240 B2
(45) Date of Patent: Mar. 3, 2020

(54) SYSTEM AND METHOD FOR CONTROLLING LEAK

(71) Applicant: KONINKLIJKE PHILIPS N.V., Eindhoven (NL)

(72) Inventors: William Anthony Truschel, Oakmont, PA (US); Kenneth E. Cole, Jr., New Alexandria, PA (US); Mark McDermott, Pittsburgh, PA (US); Ray Hoffman, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 492 days.

(21) Appl. No.: 15/520,429

(22) PCT Filed: Oct. 10, 2015

(86) PCT No.: PCT/IB2015/057761
§ 371 (c)(1),
(2) Date: Apr. 20, 2017

(87) PCT Pub. No.: WO2016/063168
PCT Pub. Date: Apr. 28, 2016

(65) Prior Publication Data
US 2017/0319812 A1 Nov. 9, 2017

Related U.S. Application Data

(60) Provisional application No. 62/068,293, filed on Oct. 24, 2014.

(51) Int. Cl.
*A61M 16/20* (2006.01)
*A61M 16/00* (2006.01)
(Continued)

(52) U.S. Cl.
CPC ........ *A61M 16/205* (2014.02); *A61M 16/024* (2017.08); *A61M 16/201* (2014.02);
(Continued)

(58) Field of Classification Search
CPC .............. A61M 16/205; A61M 16/122; A61M 16/125; A61M 16/20; A61M 16/201;
(Continued)

(56) References Cited

U.S. PATENT DOCUMENTS 3,913,607 A 10/1975 Price
5,040,532 A 8/1991 Alfery
(Continued)

FOREIGN PATENT DOCUMENTS

WO WO2013144740 A1 10/2013

*Primary Examiner* — Timothy A Stanis
*Assistant Examiner* — Cana A Gallegos
(74) *Attorney, Agent, or Firm* — Michael W. Haas (57) ABSTRACT

The present disclosure pertains to a system for controlling a leak flow rate during respiratory therapy. The system is configured to determine a leak flow rate necessary for $CO_2$ expulsion for an individual subject and facilitate control of the leak flow rate during therapy such that the system exhausts substantially the entire exhaled volume of gas during an expiration of the subject. The system facilitates control of the leak flow rate during therapy via an adjustable leak valve. Determining the leak flow rate for the subject and facilitating control of the leak rate may minimize noise from air flow in the system, minimize the power draw needed by a pressure generator of the system, reduce a loss of medicine added to the respiratory therapy gas, and/or have other advantages, while still expelling the desired amount of $CO_2$.

15 Claims, 9 Drawing Sheets

(51) Int. Cl.
*F16K 11/07* (2006.01)
*F16K 31/50* (2006.01)
*F16K 37/00* (2006.01)

(52) U.S. Cl.
CPC ........ *F16K 11/0716* (2013.01); *F16K 31/504* (2013.01); *F16K 37/0016* (2013.01); *A61M 2205/15* (2013.01); *A61M 2205/3337* (2013.01); *A61M 2205/50* (2013.01)

(58) Field of Classification Search
CPC .. A61M 39/22; A61M 16/203; A61M 16/204; A61M 16/208; A61M 16/1015; A61M 2205/15; A61M 2205/3337; F16K 11/0716; F16K 31/504; F16K 37/0016; F16K 31/445
See application file for complete search history.

(56) References Cited

U.S. PATENT DOCUMENTS

| | | |
|---|---|---|
| 6,152,129 A | 11/2000 | Berthon-Jones |
| 6,581,596 B1 | 6/2003 | Truitt |
| 6,615,831 B1 | 9/2003 | Tuitt |
| 2007/0144522 A1 | 6/2007 | Eger |
| 2010/0206310 A1 | 8/2010 | Matsubara |
| 2011/0168180 A1 | 7/2011 | Lugtigheid |
| 2011/0196251 A1 | 8/2011 | Jourdain |
| 2014/0174444 A1 | 6/2014 | Darkin |
| 2014/0283831 A1 | 9/2014 | Foote |

SYSTEM AND METHOD FOR CONTROLLING LEAK

CROSS-REFERENCE TO RELATED APPLICATIONS

This patent application claims the priority benefit under 35 U.S.C § 371 of international patent application no. PCT/IB2015/057761, filed Oct. 10, 2015, which claims the priority benefit under 35 U.S.C. § 119(e) of U.S. Provisional Application No. 62/068,293 filed on Oct. 24, 2014, the contents of which are herein incorporated by reference.

BACKGROUND OF THE INVENTION

1. Field of the Invention

The present disclosure pertains to a system and method for controlling leak during respiratory therapy.

2. Description of the Related Art

The inspiration of expired gases enriched with $CO_2$ is called rebreathing, which has short and long term adverse effects on a subject including $CO_2$ poisoning. Leak valves configured to exhaust these expired gases are known. Typically these valves allow a predetermined amount of leak at a given pressure and are not adjustable.

SUMMARY OF THE INVENTION

Accordingly, one or more aspects of the present disclosure relate to an adjustable leak valve configured to control leak during respiratory therapy. The valve comprises a tubular body, a sleeve, a dial, and/or other components. The tubular body is formed along a first axis of the valve. The tubular body has a first end, a second end, and a wall. The tubular body forms a flow path configured to conduct gas between the first end and the second end during respiratory therapy. The tubular body has body orifices formed in the wall that communicate gas from the flow path through the wall. The sleeve is rotatable about the first axis with respect to the tubular body. The sleeve substantially surrounds the body orifices in the body. The sleeve has sleeve orifices formed therein. The sleeve orifices are formed in the sleeve and are positionable to overlap with the body orifices. The dial has a tubular shape. The dial is rotatable about the first axis relative to the sleeve. The dial substantially surrounds the sleeve orifices in the sleeve. The dial has a dial orifice formed therein. The dial orifice is formed in the dial and positionable to overlap with the sleeve orifices and the body orifices. Rotational coupling between the tubular body, the sleeve, and the dial facilitates adjustable configuration of one or more properties of a leak pathway formed by positioning the overlapping of the dial orifice with at least one of the sleeve orifices and at least one of the body orifices to allow leak during respiratory therapy.

Another aspect of the present disclosure relates to a method for controlling leak during respiratory therapy with an adjustable leak valve. The valve comprises a tubular body, the tubular body extending along a first axis of the valve, the tubular body having a first end, a second end, a wall, and a flow path configured to conduct gas between the first end and the second end during respiratory therapy, the tubular body having body orifices formed in the wall that communicate gas from the flow path through the wall; a sleeve, the sleeve substantially surrounding the body orifices in the body, the sleeve having sleeve orifices formed therein, and a dial, the dial having a tubular shape, the dial substantially surrounding the sleeve orifices in the sleeve, the dial having a dial orifice formed therein. The method comprises rotating the sleeve about the first axis, the sleeve orifices being positionable to overlap with the body orifices; rotating the dial about the first axis, the dial orifice being positionable to overlap with the sleeve orifices and the body orifices; and facilitating adjustable configuration of one or more properties of a leak pathway formed by positioning the dial orifice to overlap with at least one of the sleeve orifices and at least one of the body orifices to allow leak during respiratory therapy.

Still another aspect of the present disclosure relates to a valve configured to control leak during respiratory therapy. The valve comprises means for forming a flow path, the means for forming a flow path formed along a first axis of the valve and having a first end, a second end, and a wall, the means for forming a flow path configured to conduct gas between the first end and the second end during respiratory therapy, the means for forming a flow path having body orifices formed in the wall that communicate gas from the flow path through the wall; means for substantially surrounding the body orifices, the means for substantially surrounding the body orifices rotatable about the first axis with respect to the means for forming a flow path, the means for substantially surrounding the body orifices having sleeve orifices formed therein, the sleeve orifices being formed in the means for substantially surrounding the body orifices and being positionable to overlap along the first axis with the body orifices; and means for substantially surrounding the sleeve orifices, the means for substantially surrounding the sleeve orifices having a tubular shape, the means for substantially surrounding the sleeve orifices being rotatable about the first axis with respect to the means for substantially surrounding the body orifices, the means for substantially surrounding the sleeve orifices substantially surrounding the sleeve orifices, the means for substantially surrounding the sleeve orifices having a dial orifice formed therein, the dial orifice being formed in the means for substantially surrounding the sleeve orifices and positionable to overlap with the sleeve orifices and the body orifices. Rotational coupling between the means for forming a flow path, the means for substantially surrounding the body orifices, and the means for substantially surrounding the sleeve orifices facilitates adjustable configuration of one or more properties of a leak pathway formed by positioning the overlapping of the dial orifice with at least one of the sleeve orifices and one of the body orifices to allow leak during respiratory therapy.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
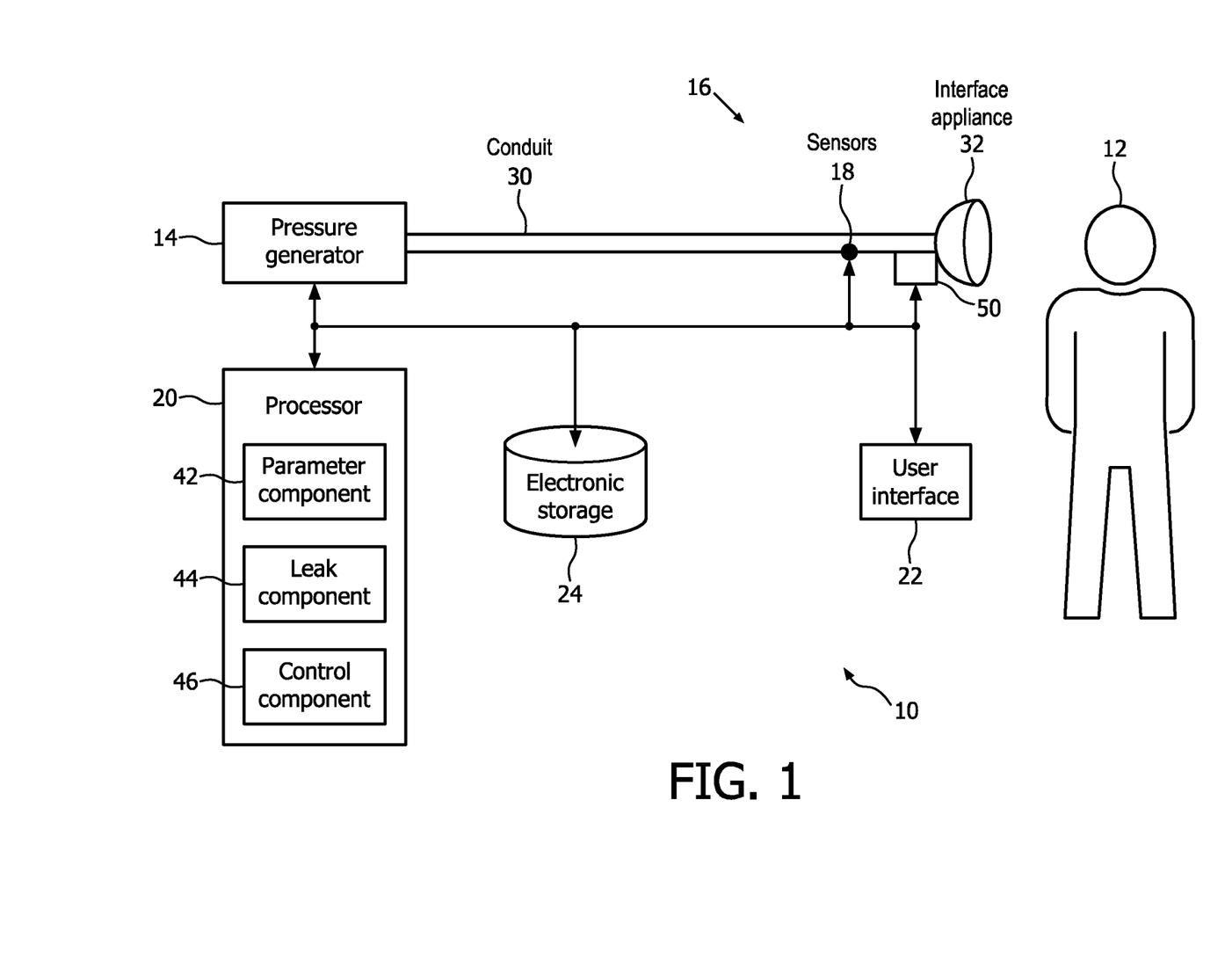
FIG. 1 illustrates a system for controlling leak during respiratory therapy.

FIG. 1 illustrates a system 10 for controlling a leak flow rate during respiratory therapy. System 10 includes a single limb ventilation circuit (though other circuits are contemplated). Leak in a single limb device is necessary to expel exhaled carbon dioxide ($CO_2$). System 10 is configured to determine a leak flow rate necessary for $CO_2$ expulsion for an individual subject 12 and facilitate control of the leak flow rate during therapy (e.g., so the leak flow rate is not excessively low or excessively high for subject 12) such that system 10 exhausts substantially the entire exhaled volume of gas during an expiration of subject 12. System 10 facilitates control of the leak flow rate during therapy via an adjustable leak valve 50. Determining the leak flow rate for subject 12 and facilitating control of the leak flow rate may minimize noise from air flow in system 10, minimize the power draw needed by a pressure generator 14 of system 10, reduce a loss of medicine added to the respiratory therapy gas, and/or have other advantages, while still expelling the desired amount of $CO_2$. In some embodiments, system 10 comprises one or more of pressure generator 14, a subject interface 16, a sensor 18, a processor 20, a user interface 22, electronic storage 24, and leak valve 50.

Pressure generator 14 is configured to generate a pressurized flow of breathable gas for delivery to the airway of subject 12. Pressure generator 14 may control one or more parameters of the flow of gas (e.g., flow rate, pressure, volume, temperature, duration, a timing, gas composition, etc.) for therapeutic purposes, and/or for other purposes. Pressure generator 14 receives a flow of gas from a gas source, such as the ambient atmosphere, and elevates and/or reduces the pressure of that gas for delivery to the airway of a patient. Pressure generator 14 is any device, such as, for example, a pump, blower, piston, or bellows, that is capable of elevating and/or reducing the pressure of the received gas for delivery to a patient. Pressure generator 14 may comprise one or more valves for controlling the pressure and/or flow of gas, for example. The present disclosure also contemplates controlling the operating speed of the blower, either alone or in combination with such valves, to control the pressure and/or flow of gas provided to the patient.

Sensors 18 are configured to generate output signals conveying information related to one or more gas parameters of the pressurized flow of breathable gas, one or more breathing parameters related to the respiration of subject 12, and/or other information. The one or more gas parameters and/or the one or more breathing parameters may comprise one or more of a flow rate, a volume, a pressure, a composition (e.g., concentration(s) of one or more constituents), temperature, humidity, acceleration, velocity, acoustic parameters, parameters indicative of respiratory effort by subject 12, a timing, a duration, a frequency, and/or other parameters. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters). Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, in communication with subject 12, and/or in other locations.

Subject interface 16 is configured to deliver the pressurized flow of breathable gas to the airway of subject 12. As such, subject interface 16 comprises a conduit 30, an interface appliance 32, and/or other components. Conduit 30 is configured to convey the pressurized flow of gas to interface appliance 32. Conduit 30 may be a flexible length of hose, or other conduit, that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12

(e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Figure 2:
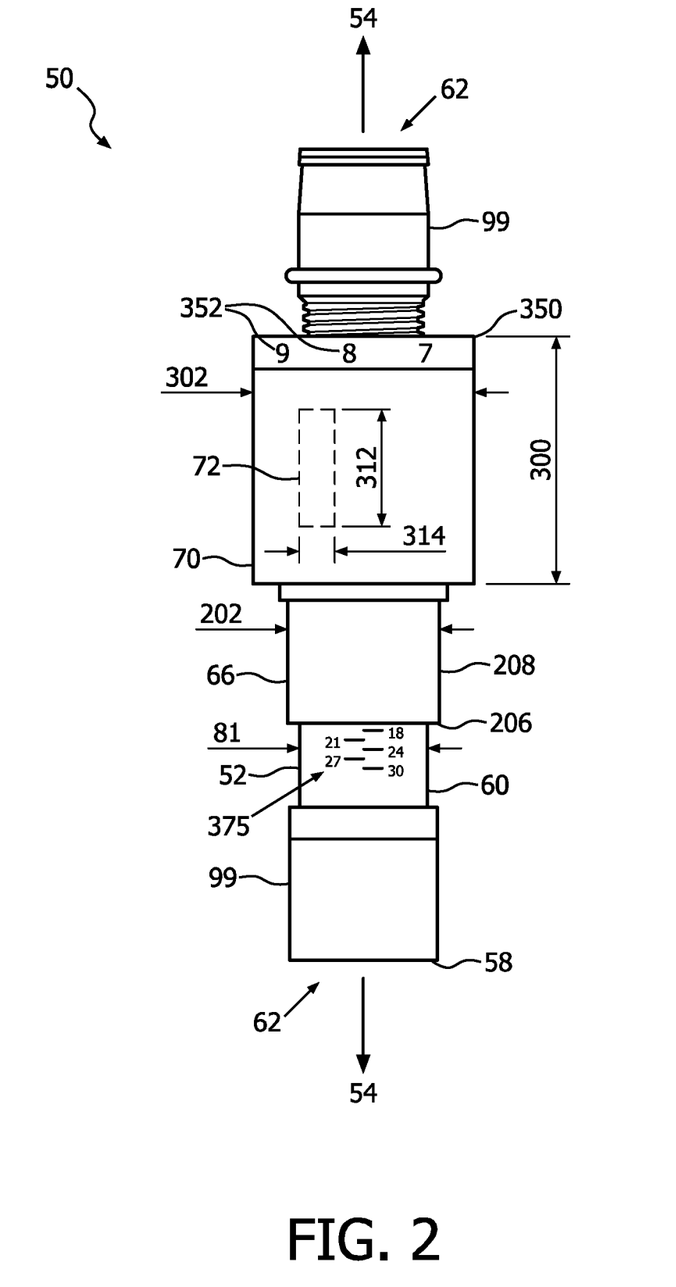
FIG. 2 illustrates an assembled view of a leak valve.
Figure 3:
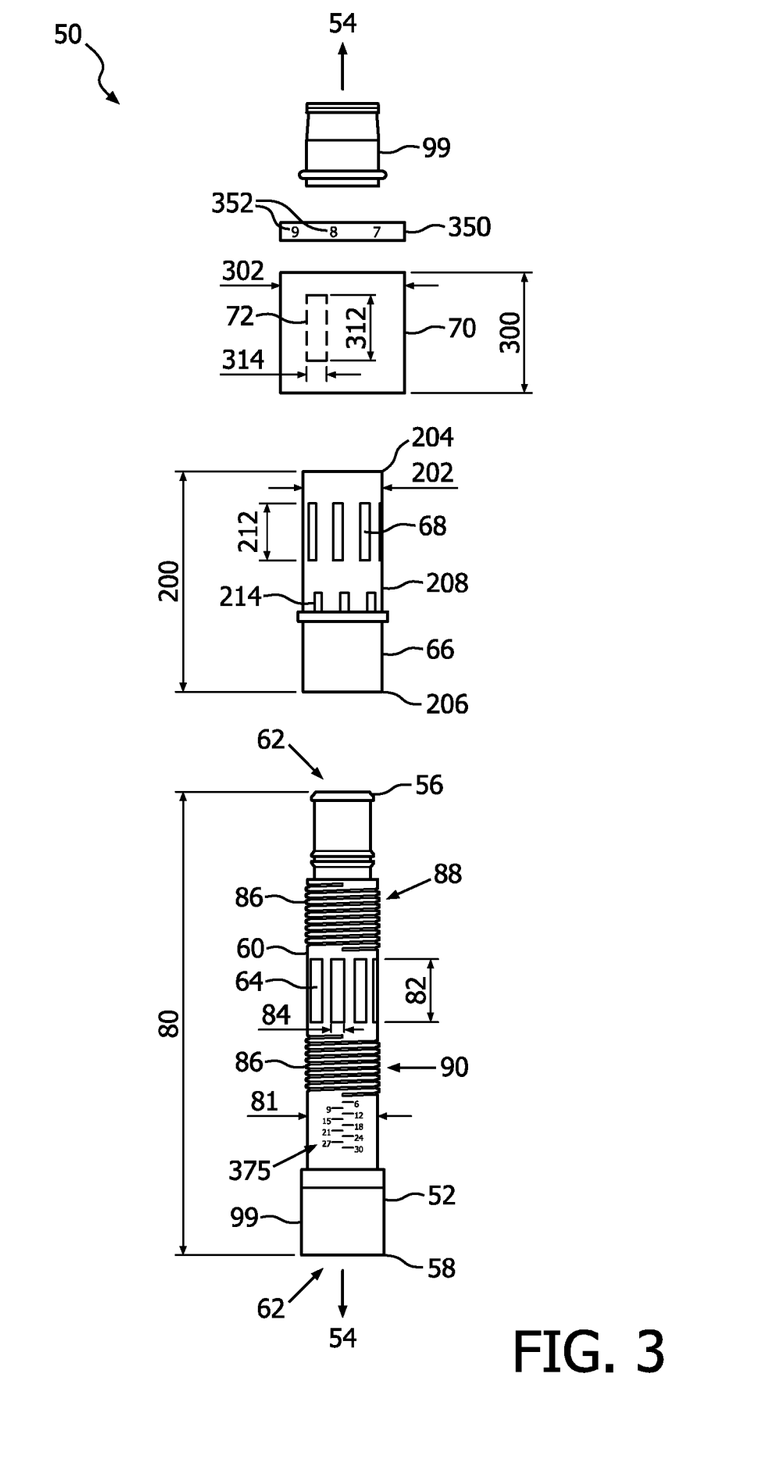
FIG. 3 illustrates an exploded view of the leak valve.

Leak valve 50 is configured to control leak during respiratory therapy. An assembled view of valve 50 is illustrated in FIG. 2. FIG. 3 illustrates an exploded view of leak valve 50. As shown in FIG. 2 and FIG. 3, leak valve 50 includes a tubular body 52, a sleeve 66, a dial 70, and/or other components. Tubular body 52 is formed along a first axis 54 of valve 50. Tubular body 52 is generally tube shaped and has a length 80 along first axis 54 of about 5 inches. In some embodiments, length 80 may be between about 3 inches and about 7 inches. Tubular body 52 has a diameter 81 of about 0.8 inches. In some embodiments, diameter 81 may be between about 0.5 inches and about 1.5 inches. Tubular body 52 has a first end 56, a second end 58 (FIG. 3), a wall 60, and/or other components. Tubular body 52 forms a flow path 62 configured to conduct gas between first end 56 and second end 58 during respiratory therapy. Tubular body 52 has body orifices 64 (FIG. 3) formed in wall 60 that communicate gas from flow path 62 through wall 60. Body orifices 64 are generally rectangular in shape, with a length 82 (FIG. 3) running along first axis 54 of about 0.7 inches and a width 84 (FIG. 3) running along a circumference of tubular body 52 of about 0.2 inches. In some embodiments, length 82 may be between about 0.5 and about 0.9 inches and width 84 may be between about 0.1 and about 0.3 inches. The shapes and sizes of tubular body 52 and/or features of tubular body 52 (e.g., body orifices 64) illustrated in FIG. 2 and FIG. 3 and described above are not intended to be limiting. Tubular body 52 and/or features of tubular body 52 may have any shape and/or size that allows tubular body 52 to function as described herein.

In some embodiments, tubular body 52 includes features 86 (FIG. 3) configured to facilitate coupling (e.g., rotatable and/or other coupling) with sleeve 66 and/or other components. In some embodiments, features 86 include threads and/or other features. Features 86 may be located in one or more locations on tubular body 52. For example, as illustrated in FIG. 3, features 86 are located in a first location 88 toward first end 56 and a second location 90 toward second end 58.

Sleeve 66 is rotatably coupled (e.g., rotatable) about first axis 54 with tubular body 52 along first axis 54 such that sleeve 66 substantially surrounds body orifices 64 in tubular body 52. Sleeve 66 is generally cylindrically shaped and has a length 200 (FIG. 3) along first axis 54 of about 2.5 inches and a diameter 202 of about 0.95 inches. In some embodiments length 200 is between about 2 inches and about 3 inches. In some embodiments, diameter 202 is between about 0.5 inches and about 1.5 inches. Sleeve 66 has a first end 204 (FIG. 3), a second end 206, a wall 208, and/or other components. Sleeve 66 has sleeve orifices 68 (FIG. 3) formed in wall 208. Sleeve orifices 68 are formed in sleeve 66 to overlap along first axis 54 with body orifices 64. Sleeve orifices 68 are positionable to overlap with the body orifices. Sleeve orifices 68 are generally rectangular in shape, with a length 212 (FIG. 3) running along first axis 54 and a width running along a circumference of sleeve 66. In some embodiments, individual sleeve orifices 68 have different cross-sectional areas that correspond to individual positive end expiratory pressures (PEEP). In some embodiments, there are nine (this is not intended to be limiting) individual sleeve orifices 68. The quantity, shapes, and/or sizes of sleeve 66 and/or features of sleeve 66 (e.g., sleeve orifices 68) illustrated in FIG. 2 and FIG. 3 and described above are not intended to be limiting. Sleeve 66 and/or features of sleeve 66 may have any shape and/or size, in any quantity, that allows sleeve 66 to function as described herein.

In some embodiments, sleeve 66 includes features 214 (FIG. 3) configured to facilitate coupling (e.g., rotatable and/or other coupling) with tubular body 52, dial 70, and/or other components of valve 50. In some embodiments, features 214 include threads (e.g., on an inside surface of sleeve 66 that correspond to the threads on tubular body 52), detents (e.g., that correspond to individual ones of sleeve orifices 68 and/or features in dial 70) and/or other features. Features 214 may be located in one or more locations on sleeve 66. For example, as illustrated in FIG. 3, detent features 214 are located toward second end 206 along first axis 54 relative to sleeve orifices 68.

Dial 70 is generally tube shaped and has a length 300 along first axis 54 of about 1.38 inches and a diameter 302 of about 1.41 inches. In some embodiments, length 300 and/or diameter 302 may be between about 1 inch and about 2 inches. Dial 70 is rotatably coupled about first axis 54 with sleeve 66 along first axis 54 such that dial 70 substantially surrounds sleeve orifices 68 in sleeve 66. Dial 70 has a dial orifice 72 formed therein. Dial orifice 72 is formed in dial 70 to overlap along first axis 54 with sleeve orifices 68 and body orifices 64. Dial orifice is positionable to overlap with sleeve orifices 68 and/or body orifices 64, and/or other components of valve 50. Dial orifice 72 is generally rectangular in shape, with a length 312 (FIG. 3) of about 0.7 inches running along first axis 54 and a width 314 of about 0.15 inches running along a circumference of sleeve 66. In some embodiments, length 312 is between about 0.5 inches and about 1 inch. In some embodiments, width 314 is between about 0.1 inches and about 0.2 inches. In some embodiments, dial 70 includes features configured to facilitate coupling (e.g., rotatable and/or other coupling) with sleeve 66, and/or other components of valve 50. In some embodiments, these features may include detent features (e.g., on an inside surface of dial 70 that correspond to the detent features on sleeve 66) and/or other features. These features may be located in one or more locations on sleeve dial 70. The shapes and sizes of dial 70 and/or features of dial 70 (e.g., dial orifice 72) illustrated in FIG. 2 and FIG. 3 and described above are not intended to be limiting. Dial 70 and/or features of dial 70 may have any shape and/or size that allows sleeve 66 to function as described herein.

In some embodiments, valve 50 may include one or more components 99 configured to facilitate coupling valve 50 with one or more components of subject interface 16 (FIG. 1). For example, components 99 may include a swivel, a nipple, a barb, a fastener, a pipe coupling, and/or other coupling components.

Rotational coupling between tubular body 52, sleeve 66, and dial 70 facilitates adjustable configuration of one or more properties of a leak pathway formed by overlapping dial orifice 72 with one of the sleeve orifices 68 and one of the body orifices 64 to allow leak during respiratory therapy. In some embodiments, tubular body 52, sleeve 66, and dial 70 are configured such that the one or more properties of the leak pathway include a cross-sectional area of the leak pathway. In some embodiments, tubular body 52, sleeve 66, and dial 70 are configured such that the cross-sectional area of the leak pathway corresponds to one or more of a PEEP pressure, a leak flow rate, and/or other parameters.

For example, sleeve 66 may be threaded onto tubular body 52. Dial 70 may be slip fit over sleeve 66 and detented to sleeve 66 such that dial 70 may freely rotate (subject to the detents) about sleeve 66. A PEEP level indicator 350 may be fixedly coupled with sleeve 66 such that PEEP levels 352 indicated on PEEP level indicator 350 correspond to sleeve orifices 68 of different sizes, and such that dial 70 may still freely rotate on sleeve 66. Dial orifice 72 may be aligned with one of the PEEP level indicators 352 (e.g., a desired and/or prescribed PEEP level), which uncovers a corresponding one (and/or a portion of a corresponding one) of the sleeve orifices 68. While the rotational alignment between dial orifice 72 and one of the sleeve orifices 68 is maintained (e.g., via detents), sleeve 66 may be rotated on tubular body 52 such that aligned dial orifice 72/sleeve orifice 68 uncover (and/or cover) one or more of the body orifices 64 (wholly and/or partially) to form a leak pathway that facilitates leak at a specific flow rate (e.g., corresponding to the cross-sectional area of the flow pathway). The specific leak flow rate may be indicated via a leak flow rate scale 375 marked on tubular body 52 and/or by other indicators. The specific leak flow rate may be indicated by the location of second end 206 of sleeve 66 on leak flow rate scale 375. In FIG. 2, the leak flow rate indicated is 15 LPM, for example.

Figure 4:
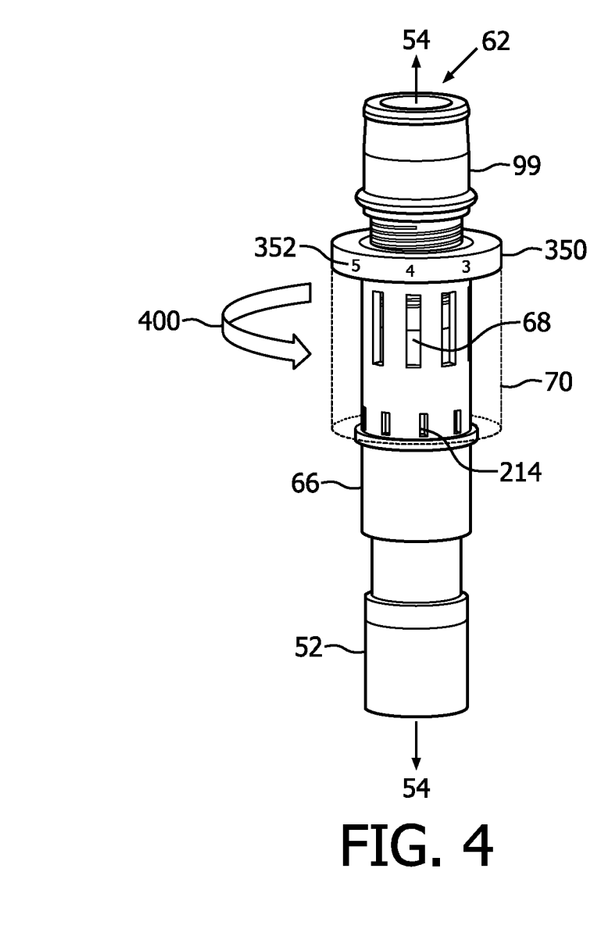
FIG. 4 illustrates rotational alignment of a dial orifice with a sleeve orifice.
Figure 5:
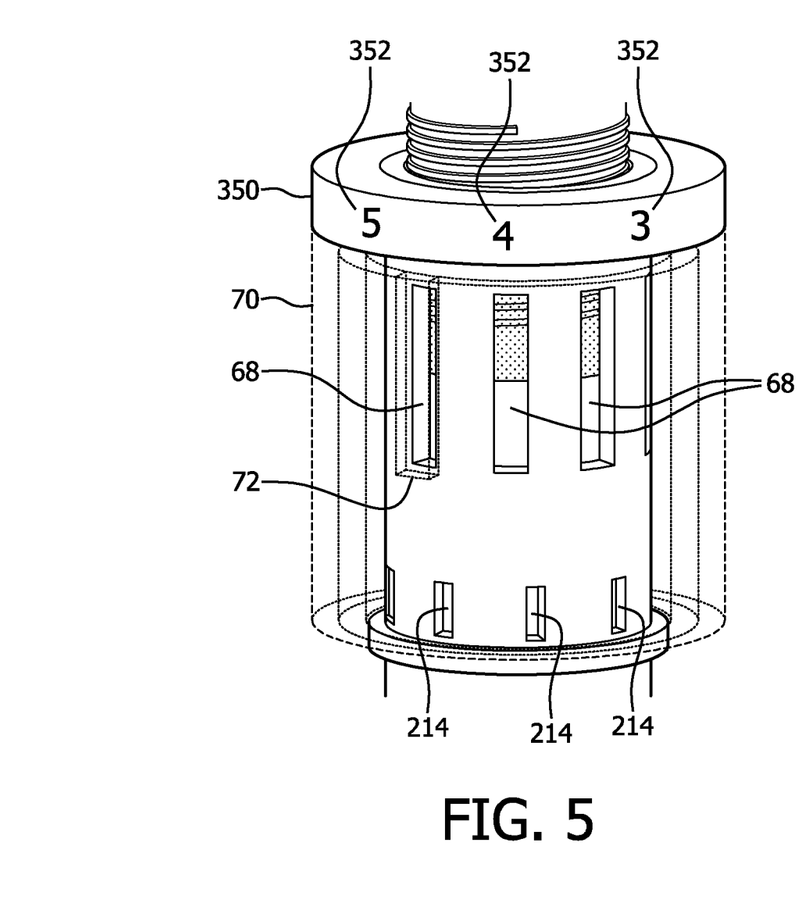
FIG. 5 illustrates rotational alignment of the dial orifice with a sleeve orifice.

FIG. 4 and FIG. 5 illustrate rotational 400 alignment of dial orifice 72 with one of the sleeve orifices 68. Dial orifice 72 may be rotated 400 (FIG. 4) such that it becomes aligned with one of the PEEP level indicators 352 (e.g., a desired and/or prescribed PEEP level), which uncovers a corresponding one (and/or a portion of a corresponding one) of the sleeve orifices 68 (FIG. 5). Dial 70 and dial orifice 72 are shown in FIG. 4 and FIG. 5 as wireframe outlines so that sleeve 66 and sleeve orifices 68 are visible for illustration.

Figure 6A:
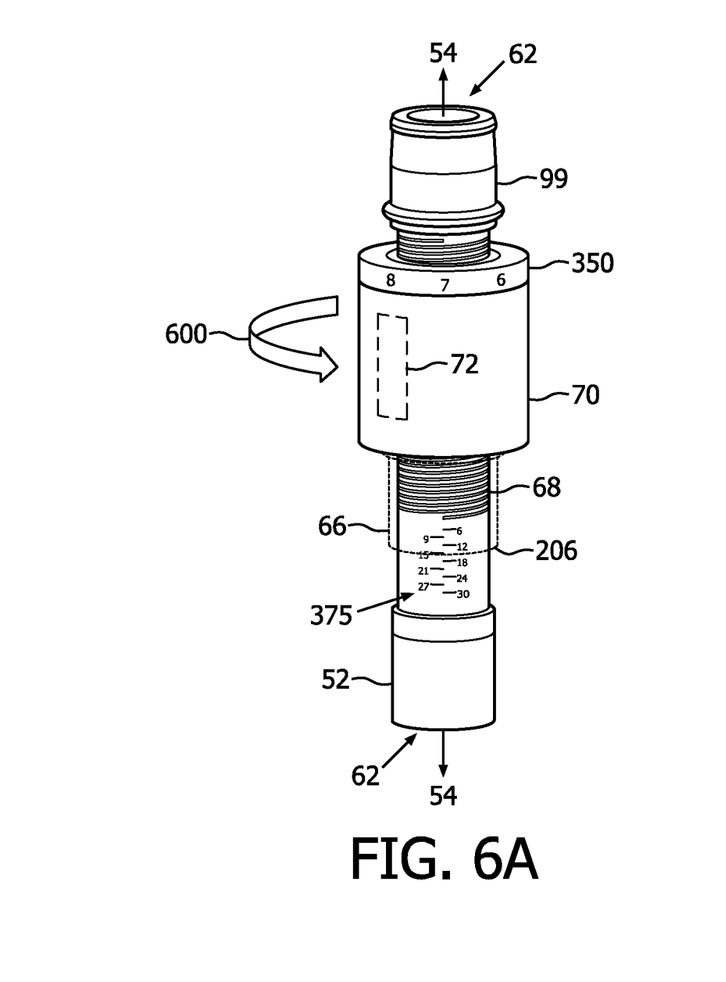
FIG. 6A illustrates rotation of the sleeve and dial on a tubular body.
Figure 6B:
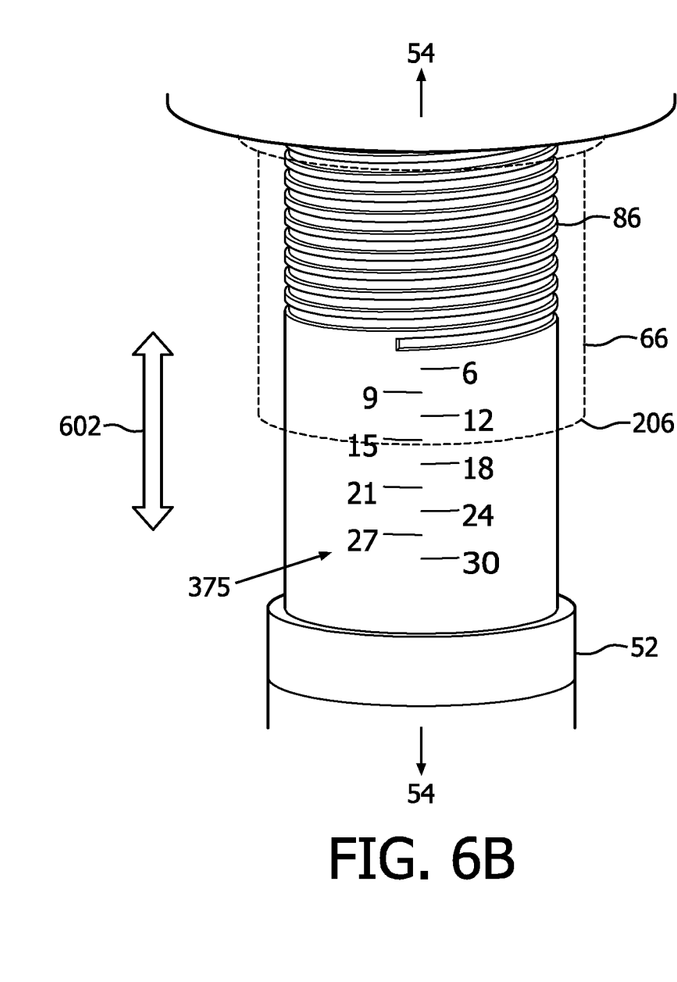
FIG. 6B illustrates travel of the sleeve along a first axis of the tubular body.

FIG. 6A illustrates rotation 600 of sleeve 66 and dial 70 on tubular body 52. FIG. 6B illustrates travel 602 of sleeve 66 along first axis 54 on tubular body 52. As described above, sleeve 66 may be threaded (e.g., via features 86) onto tubular body 52. While the rotational alignment between dial orifice 72 and one of the sleeve orifices 68 (shown in FIG. 4 and FIG. 5) is maintained (e.g., via detents), sleeve 66 may be rotated on tubular body 52 such that aligned dial orifice 72/sleeve orifice 68 uncover (and/or cover) one or more of the body orifices 64 (not shown) to form a leak pathway that facilitates leak at a specific flow rate (e.g., corresponding to the cross-sectional area of the flow pathway). Rotating sleeve 66 in one direction (e.g., clockwise) causes sleeve 66 to travel toward second end 206 along first axis 54 and rotating sleeve 66 in the opposite direction (e.g., counter clockwise) causes sleeve 66 to travel toward first end 204 (shown in FIG. 3) along first axis 54. The specific leak flow rate may be indicated via a leak flow rate scale 375 marked on tubular body 52 and/or by other indicators. The specific leak flow rate may be indicated by the location of second end 206 of sleeve 66 on leak flow rate scale 375. In FIG. 6B, the leak flow rate indicated is 15 LPM, for example.

Figure 7A:
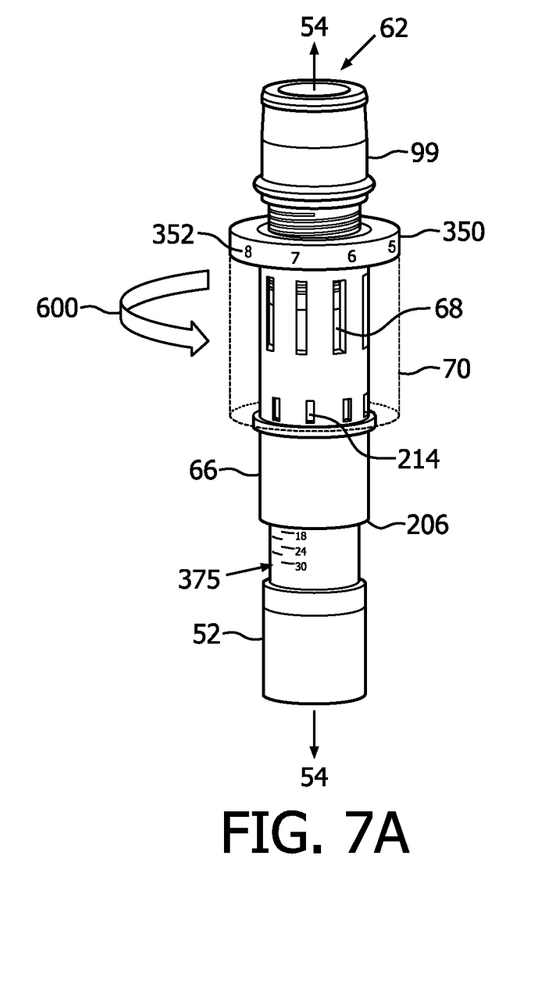
FIG. 7A illustrates a flow path formed by overlapping the dial orifice with one of the sleeve orifices and one of the body orifices.
Figure 7B:
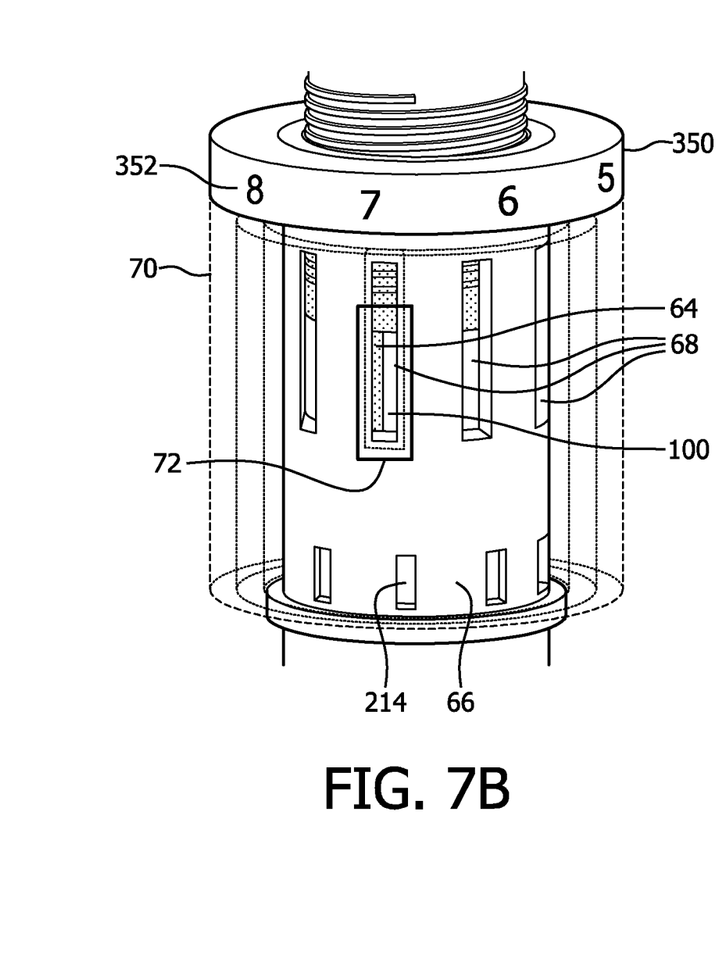
FIG. 7B illustrates the flow path formed by overlapping the dial orifice with one of the sleeve orifices and one of the body orifices.

FIGS. 7A and 7B illustrate flow path 100 formed by overlapping dial orifice 72 with one of the sleeve orifices 68 and one of the body orifices 64. Rotational coupling between tubular body 52, sleeve 66, and dial 70 facilitates adjustable configuration of one or more properties of leak pathway 100. The one or more properties of leak pathway 100 include a cross-sectional area of the leak pathway and/or other properties. In some embodiments, tubular body 52, sleeve 66, and dial 70 are configured such that the cross-sectional area of the leak pathway corresponds to one or more of a PEEP pressure (e.g., as indicated by alignment of dial orifice 72 with PEEP levels 352 indicated on PEEP level indicator 350), a leak flow rate (e.g., as indicated by the position of second end 206 of sleeve 66 on leak flow rate scale 375), and/or other parameters.

Figure 8:
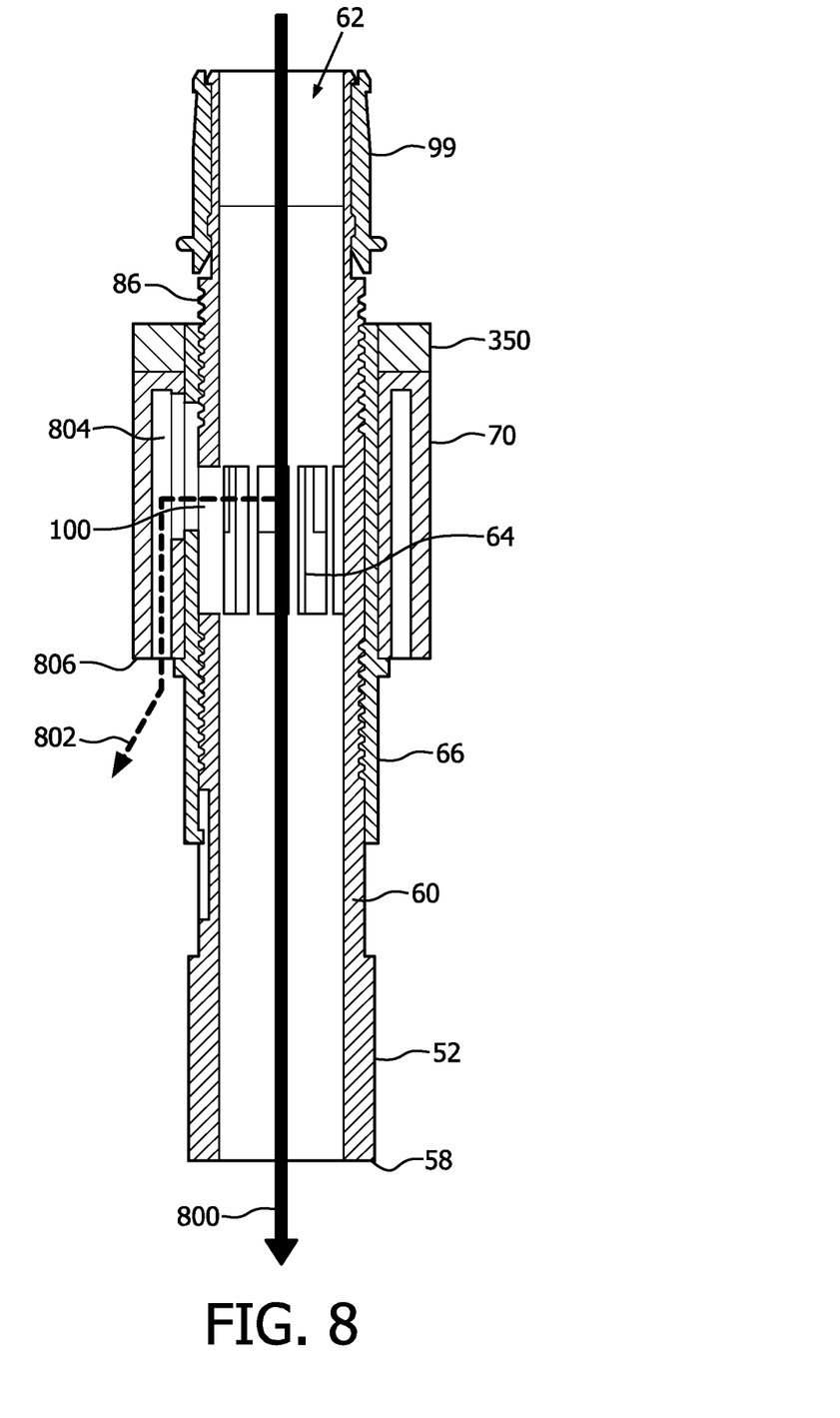
FIG. 8 illustrates gas flow through the leak valve during exhalation of a subject.

FIG. 8 illustrates gas flow 800 through valve 50 during exhalation of subject 12 (FIG. 1). Valve 50 is configured to exhaust substantially the entire exhaled volume of gas during an expiration of subject 12. Exhaled gas may flow through flow pathway 62. Leaked gas 802 flows through leak pathway 100 to the ambient environment. In some embodiments, as shown in FIG. 8, dial 70 is configured such that dial orifice 72 is formed on an inside surface of dial 70 and allows leaked gas to flow into an internal cavity 804 within a wall of dial 70 before flowing out to the ambient environment 806. The cross-sectional area of cavity 804 is larger than the cross section area of leak pathway 100 so as not to limit the flow rate of leaked gas through leak pathway 100. Leaked gas 802 flows into cavity 804 so that the exhausted leaked gas 802 is directed away from the subject (e.g., subject 12).

Returning to FIG. 1, processor 20 is configured to provide information processing capabilities in system 10. As such, processor 20 may comprise one or more of a digital processor, an analog processor, or a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory pressure generator 14, user interface 22), or processor 20 may represent processing functionality of a plurality of devices operating in coordination.

As shown in FIG. 1, processor 20 is configured to execute one or more computer program components. The one or more computer program components may comprise one or more of a parameter component 42, a leak component 44, a control component 46, and/or other components. Processor 20 may be configured to execute components 42, 44, and/or 46 by software; hardware; firmware; some combination of software, hardware, and/or firmware; and/or other mechanisms for configuring processing capabilities on processor 20.

It should be appreciated that although components 42, 44, and 46 are illustrated in FIG. 1 as being co-located within a single processing unit, in embodiments in which processor 20 comprises multiple processing units, one or more of components 42, 44, and/or 46 may be located remotely from the other components. The description of the functionality provided by the different components 42, 44, and/or 46 described below is for illustrative purposes, and is not intended to be limiting, as any of components 42, 44, and/or 46 may provide more or less functionality than is described. For example, one or more of components 42, 44, and/or 46 may be eliminated, and some or all of its functionality may be provided by other components 42, 44, and/or 46. As another example, processor 20 may be configured to execute one or more additional components that may perform some or all of the functionality attributed below to one of components 42, 44, and/or 46.

Parameter component 42 is configured to determine one or more parameters within system 10. The one or more parameters within system 10 may comprise gas parameters related to the pressurized flow of breathable gas, breathing parameters related to the respiration of subject 12, and/or other parameters. Parameter component 42 is configured to determine the one or more parameters based on the output signals of sensors 18, and/or other information. The one or more gas parameters of the pressurized flow of breathable gas may comprise, for example, one or more of a flow rate, a volume (e.g., a tidal volume, a minute volume, etc.), a pressure, humidity, temperature, acceleration, velocity, and/or other gas parameters. For example, the one or more gas parameters may include a minute volume. The minute volume may be the amount of expired gas (such as 10 liters per minute) that is enriched with CO2 and therefore relates to a specification for the leak flow rate to expel gas prior to the next inspiration to prevent rebreathing. It may be a measurement of the total volume of gas exiting the lungs per minute. The one or more breathing parameters may include, for example, a tidal volume, a composition, a timing (e.g., beginning and/or end of inhalation, beginning and/or end of exhalation, etc.), a duration (e.g., of inhalation, of exhalation, of a single breathing cycle, an inspiratory time, an expiratory time, a full breath time, etc.), a breath rate, a respiration frequency (e.g., a respiratory rate), a parameter indicative of respiratory effort, and/or other parameters. The information determined by parameter component 42 may be used for controlling pressure generator 14, stored in electronic storage 24, and/or used for other uses.

Leak component 44 is configured to determine a cross-sectional area for the leak pathway 100 (FIGS. 7A and 7B) formed by overlapping the dial orifice 72 (FIGS. 7A and 7B) with one of the sleeve orifices 68 (FIGS. 7A and 7B) and one of the body orifices 64 (FIGS. 7A and 7B) for subject 12. Leak component 44 is configured to determine the cross-sectional area based on the output signals from sensors 18, the parameters determined by parameter component 42, information stored in electronic storage 24, information entered and/or received via user interface 22, and/or other information. In some embodiments, leak component 44 is configured to determine a leak flow rate ($Q_{leak}$) for subject 12 that substantially prevents rebreathing of exhaled $CO_2$ enriched gas, obtain a prescribed PEEP level for subject 12 (e.g., via entry and/or selection of the PEEP level via user interface 22 by subject 12, a doctor, a caregiver, and/or other users), and then determine the cross-sectional area for leak pathway 100 based on the determined leak flow rate, the prescribed PEEP, and/or other information.

In some embodiments, leak component 44 is configured to determine the leak flow rate ($Q_{leak}$) for subject 12 that substantially prevents rebreathing as follows (where the various parameters listed in the individual equations below are determined by parameter component 42 as described above, for example). (Parameter component 42 may be configured to monitor the volume of gas expired on individual breaths and determine average parameters—e.g., minute volume by itself is the average over one minute. The time permitted during the expiration may also be monitored and also be averaged, such that the leak parameter may be determined based on the averages with some safety margin in order to accommodate variations breath to breath.) To prevent rebreathing:

$$Q_{leak} > \frac{\text{Tidal Volume}}{\text{Expiratory Time}} \qquad (1)$$

where:

$$\text{Tidal Volume} = \frac{\text{Minute Volume}}{\text{Respiratory Rates}}. \qquad (2)$$

Substituting Equation (2) into Equation (1):

$$Q_{leak} > \frac{\text{Minute Volume}}{\text{Respiratory Rate} - \text{Expiratory Time}}. \qquad (3)$$

Leak component 44 is then configured to determine a ratio I:E, where $$I{:}E = \frac{\text{Inspiratory Time}}{\text{Expiratory Time}}. \qquad (4)$$

Therefore,

Inspiratory Time=$I{:}E$·Expiratory Time. (5)

But,

Expiratory Time=Breath Time−Inspiratory Time. (6)

And, $$\text{Breath Time} = \frac{1}{\text{Respiratory Rate}}. \qquad (7)$$

Substituting Equation (5) into Equation (6) gives:

Expiratory Time=Breath Time−($I{:}E$·Expiratory Time). (8)

Solving for Expiratory Time gives:

$$\text{Expiratory Time} = \frac{\text{Breath Time}}{(1 + I{:}E)}. \qquad (9)$$

Substituting Equation (9) into Equation (3) gives:

$$Q_{leak} > \frac{\text{Minute Volume} \cdot (1 + I{:}E)}{\text{Respiratory Rate} \cdot \text{Breath Time}}. \qquad (10)$$

But Equation (7) implies that the denominator is unity and therefore:

$Q_{leak}$>Minute Volume·(1+$I{:}E$)=MinVent$_{EET}$. (11)

MinVent$_{EET}$ is therefore the volume expired during only the expiratory time of a breath of subject 12, or equivalently, the average expiratory flow rate expressed in volume per minute. Leak component 44 is configured to determine $Q_{leak}$ (the leak flow rate) such that $Q_{leak}$ is high enough to expel substantially the entire volume expired by subject 12 during exhalation (the leak flow rate is greater than MinVent$_{EET}$).

Figure 9:
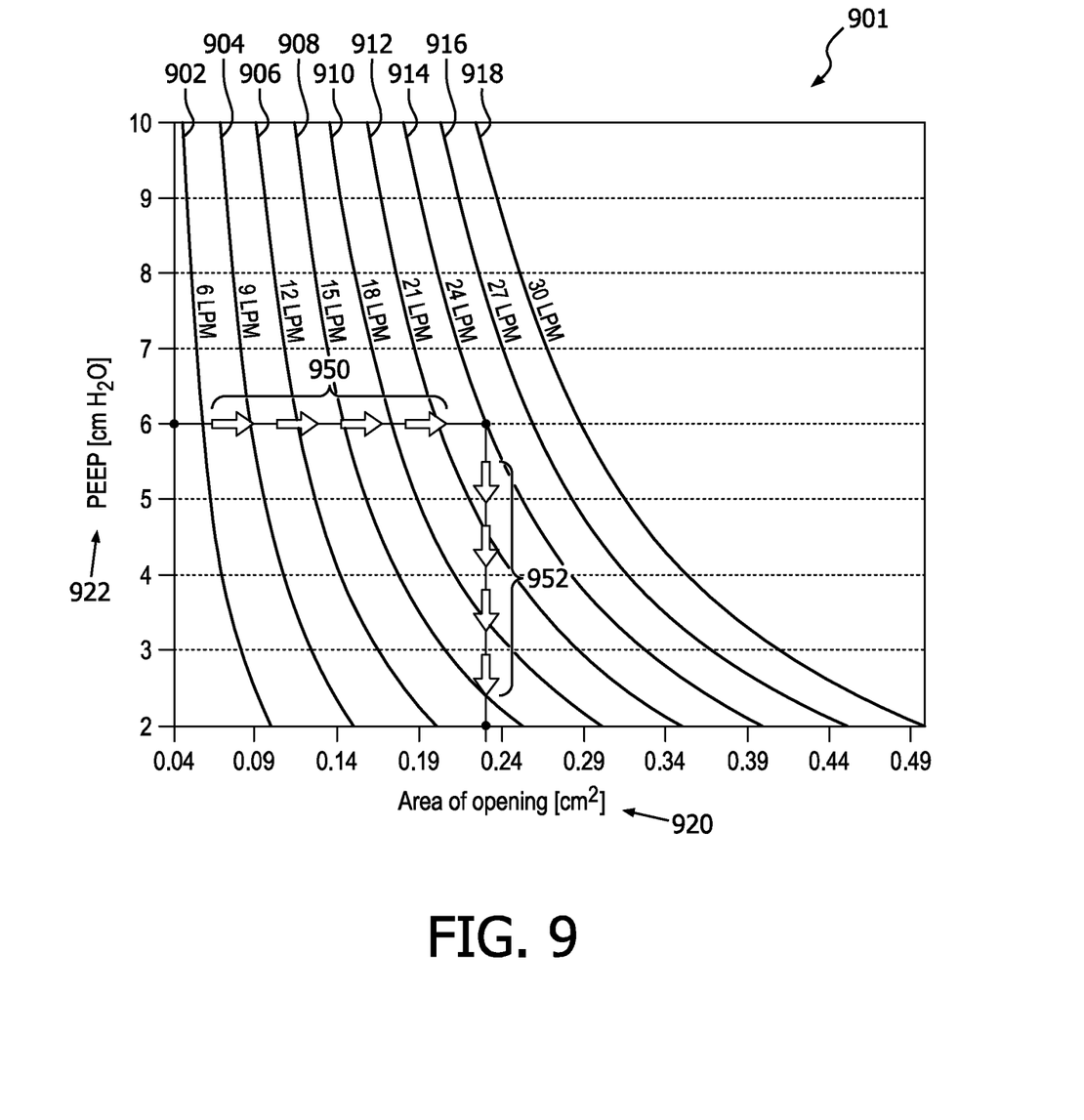
FIG. 9 illustrates a graph of expected leak flow rates from orifices having fixed cross-sectional areas at various PEEP levels determined using Bernoulli's equation.

As described above, leak component 44 is configured to determine the cross-sectional area for leak pathway 100 based on the determined leak flow rate, the prescribed PEEP level, and/or other information. FIG. 9 illustrates a graph 901 of expected leak flow rates 902-918 from orifices having a fixed cross-sectional areas 920 at various PEEP levels 922 determined using Bernoulli's equation:

$$Q_{leak} = C_d A \sqrt{\frac{PEEP}{\rho}}$$

where $Q_{leak}$ is the Expected Leak Flow Rate, $C_d$ is the discharge coefficient of a leak orifice (about 0.8 and/or empirically determined), A is the area of the leak orifice, and p is the gas density). In some implementations, leak component 44 may determine the information in FIG. 9. In some implementations, the information in FIG. 9 may be previously determined and/or stored in electronic storage 24 and accessed and/or obtained by leak component 44. Leak component 44 may determine the cross-sectional area for leak pathway 100 using the information in FIG. 9 and/or similar information along with the determined leak flow rate and the prescribed PEEP level. In some embodiments, valve 50 may include one or more screens, filters, and/or other devices configured to filter, restrict, and/or otherwise change the relationship between flow and the area of the orifice to something other than Bernoulli's equation in the various components of valve 50. In these embodiments, leak component 44 is configured to account for these and/or similar features when determining the cross-sectional area for leak pathway 100.

By way of a non-limiting example, for a subject (e.g., subject 12) with a 400 ml Tidal Volume who is breathing at 30 breaths per minute with an I:E ratio of 1:1 and a prescribed PEEP of 6 cm H2O leak component 44 may determine a $Q_{leak}$ of 24 liters per minute (LPM) based on the equations above and an orifice size of about 0.22 cm² based on the information in FIG. 9. By way of visual illustration on FIG. 9, tracking 950 from a PEEP level of 6 cm H2O across graph 901 until reaching expected leak flow rate 914 that corresponds to 24 LPM results 952 in an orifice size of about 0.22 cm².

Control component 46 is configured to control pressure generator 14 to generate the flow of gas in accordance with a positive pressure support therapy regime. In positive airway pressure support therapy the pressurized flow of gas generated by the pressure generator is controlled to replace and/or compliment a patient's regular breathing. Positive airway pressure support therapy may be used to maintain an open airway in a patient so that oxygen and carbon dioxide may be exchanged more easily, requiring little and/or no effort from the patient. By way of non-limiting example, control component 46 may control pressure generator 14 such that the pressure support provided to the subject via the flow of gas comprises continuous positive airway pressure support (CPAP), bi-level positive airway pressure support (BPAP), proportional positive airway pressure support (PPAP), ventilation therapy, and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) to promote or assist tidal ventilation. In some therapy modes (e.g., PPAP), control component 46 may control pressure generator 14 to apply variable pressure support in which the amount of pressure delivered to the patient during inhalation and/or during exhalation is determined and delivered on a breath by breath basis. In some embodiments, control component 46 may be configured to control pressure generator 14 to temporarily drop the supplied pressure during exhalation (C-Flex, Airway Pressure Release Ventilation (APRV)) to reduce exhalation effort required by the patent.

In some embodiments, control component 46 is configured to facilitate controlled minute volume, tidal volume guarantee, etc.

In some embodiments, control component 46 is configured to control pressure generator 14 to deliver staged pressure support. In staged pressure support therapy, the pressure delivered by pressure generator 14 gradually increases over time. In some embodiments, control component 46 may control pressure generator 14 to switch therapy modes based on information related to the respiration of subject 12 and/or other information. For example, control component 46 may control pressure generator 54 to change from BPAP to CPAP after a certain number of breaths by subject 12 and/or by some external monitor, caregiver and/or alert, such as in rescue and/or apnea ventilation.

Control component 46 is configured to control pressure generator 14 based on information related to the output signals from sensors 18, information determined by parameter component 42, information determined by leak component 44, information entered by a user to user interface 22, and/or other information.

In some embodiments, sleeve 66 and/or dial 70 may be manually rotated by a user. In some embodiments, control component 46 is configured to control rotation of sleeve 66 (FIG. 2) and/or dial 70 (FIG. 2). In some embodiments, valve 50 may include one or more motors (not shown) and/or other actuators configured to rotate sleeve 66 and/or dial 70 on tubular body 52 (FIG. 2). In some embodiments, control component 46 is configured to control the one or more motors and/or actuators to cause rotation of sleeve 66 and/or dial 70 such that a leak pathway having the cross sectional area determined by leak component 44 is formed. In some embodiments, control component 46 may control rotation based on the information determined by leak component 44, the sizes of the orifices in tubular body 52, sleeve 66, and dial 70, information entered and/or selected via user interface 22, a prescribed PEEP level, information related to the output signals from sensors 18, information determined by parameter component 42, and/or based on other information.

In some embodiments, a sleeve and/or filter may be replaced over a constant or nearly constant orifice area to alternatively control and/or partially control the leak characteristics of valve 50.

User interface 22 is configured to provide an interface between system 10 and subject 12 and/or other users through which subject 12 and/or other users may provide information to and receive information from system 10. Other users may comprise a caregiver, a doctor, a decision maker, and/or other users. This enables data, cues, results, and/or instructions and any other communicable items, collectively referred to as "information," to be communicated between a user (e.g., subject 12) and one or more of pressure generator 14, processor 20, valve 50, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

Electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, pressure generator 14, etc.). Information determined by processor 20 and/or stored by electronic storage 24 may comprise information related to respiration of subject 12, information related to leak (e.g., a cross-sectional area of the leak flow path), and/or other information. The information stored by electronic storage 24 may be viewed via user interface 22, via a separate computer wirelessly (and/or with wires) coupled with system 10, and/or other via other methods. The information stored by electronic storage 24 may be used, for example, to adjust settings, used by a doctor to make medical decisions, and/or for other uses.

Figure 10:
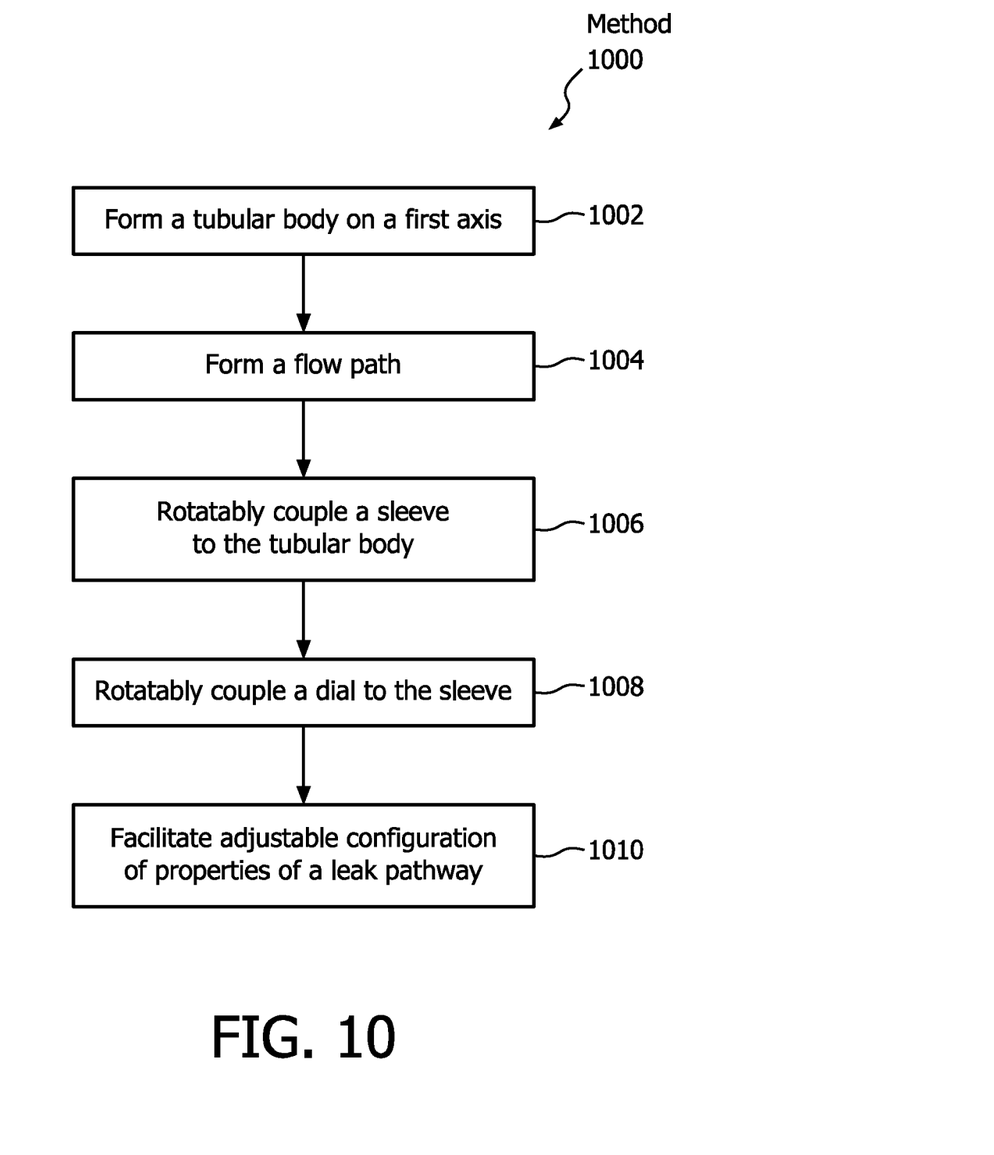
FIG. 10 illustrates a method for controlling leak during respiratory therapy with an adjustable leak valve.

FIG. 10 illustrates a method for controlling leak during respiratory therapy with an adjustable leak valve. The valve comprises a tubular body, a sleeve, a dial, and/or other components. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, one or more operations of method 1000 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1002, the tubular body is formed on a first axis of the valve. The tubular body has a first end, a second end, and a wall. In some embodiments, operation 1002 is performed by a tubular body the same as or similar to tubular body 52 (shown in FIG. 2 and described herein).

At an operation 1004, a flow path is formed. The flow path is formed with the tubular body and configured to conduct gas between the first end and the second end of the tubular body during respiratory therapy. The tubular body has body orifices formed in the wall that communicate gas from the flow path through the wall. In some embodiments, operation 1004 is performed by a tubular body the same as or similar to tubular body 52 (shown in FIG. 2 and described herein).

At an operation 1006, the sleeve is rotatably coupled to the tubular body. The sleeve is rotatably coupled about the first axis along the first axis such that the sleeve substantially surrounds the body orifices in the body. The sleeve has sleeve orifices formed therein. The sleeve orifices are formed in the sleeve to overlap along the first axis with the body orifices. Individual sleeve orifices have different cross-sectional areas that correspond to individual PEEP pressures. In some embodiments, operation 1006 is performed by a sleeve the same as or similar to sleeve 66 (shown in FIG. 2 and described herein).

At an operation 1008, the dial is rotatably coupled to the sleeve. The dial is rotatably coupled to the sleeve about the first axis along the first axis such that the dial substantially surrounds the sleeve orifices in the sleeve. The dial has a tubular shape. The dial has a dial orifice formed therein. The dial orifice is formed in the dial to overlap along the first axis with the sleeve orifices and the body orifices. In some embodiments, operation 1008 is performed by a dial the same as or similar to dial 70 (shown in FIG. 2 and described herein).

At an operation 1010, a leak pathway is formed by facilitating adjustable configuration (e.g., rotation) of the sleeve and the dial. Properties of the leak pathway are adjustable. The leak pathway is formed by overlapping the dial orifice with one of the sleeve orifices and one of the body orifices via rotational coupling between the tubular body, the sleeve, and the dial to allow leak during respiratory therapy. One or more properties of the leak pathway include a cross-sectional area of the leak pathway. The cross-sectional areal of the leak pathway may correspond to one or more of a PEEP pressure or a leak flow rate. In some embodiments, one or more processors may determine a cross-sectional area for the leak pathway and control rotation of the sleeve and the dial based on the determined cross-sectional area. In some embodiments, operation 1010 is performed by tubular body, a sleeve, and a dial the same as or similar to tubular body 52, sleeve 66, and dial 70 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. An adjustable leak valve configured to control leak during respiratory therapy, the valve comprising:
   a tubular body formed along a first axis of the valve having a first end, a second end, and a wall, the tubular body forming a flow path configured to conduct gas between the first end and the second end during respiratory therapy, the tubular body having body orifices formed in the wall that communicate gas from the flow path through the wall;
   a sleeve rotatable about the first axis with respect to the tubular body, the sleeve substantially surrounding the body orifices in the body, the sleeve having sleeve orifices formed therein, the sleeve orifices being formed in the sleeve and being positionable to overlap with the body orifices; and
   a dial having a tubular shape, the dial being rotatable about the first axis relative to the sleeve, the dial substantially surrounding the sleeve orifices in the sleeve, the dial having a dial orifice formed therein, the dial orifice being formed in the dial and positionable to overlap with the sleeve orifices and the body orifices, wherein a rotational coupling between the tubular body, the sleeve, and the dial facilitates adjustable configuration of one or more properties of a leak pathway formed by positioning the overlapping of the dial orifice with at least one of the sleeve orifices and at least one of the body orifices to allow leak during respiratory therapy.

2. The valve of claim 1, wherein the tubular body, the sleeve, and the dial are configured such that the one or more properties of the leak pathway include a cross-sectional area of the leak pathway.

3. The valve of claim 2, wherein the tubular body, the sleeve, and the dial are configured such that the cross-sectional area of the leak pathway corresponds to one or more of a positive end expiratory pressure (PEEP) or a leak flow rate.

4. The valve of claim 1, wherein the sleeve is configured such that individual sleeve orifices have different cross-sectional areas that correspond to individual positive end expiratory pressures (PEEP).

5. The valve of claim 1, wherein rotation of the sleeve and the dial is caused by one or more physical computer processors, the one or more physical computer processors configured to determine a cross-sectional area for the leak pathway and control rotation of the sleeve and the dial based on the determined cross-sectional area.

6. A method for controlling leak during respiratory therapy with an adjustable leak valve, the valve comprising:
   a tubular body, the tubular body extending along a first axis of the valve, the tubular body having a first end, a second end, a wall, and a flow path configured to conduct gas between the first end and the second end during respiratory therapy, the tubular body having body orifices formed in the wall that communicate gas from the flow path through the wall;
   a sleeve, the sleeve substantially surrounding the body orifices in the body, the sleeve having sleeve orifices formed therein, and
   a dial, the dial having a tubular shape, the dial substantially surrounding the sleeve orifices in the sleeve, the dial having a dial orifice formed therein;
   the method comprising:
      rotating the sleeve about the first axis, the sleeve orifices being positionable to overlap with the body orifices;
      rotating the dial about the first axis, the dial orifice being positionable to overlap with the sleeve orifices and the body orifices; and
      facilitating adjustable configuration of one or more properties of a leak pathway formed by positioning the dial orifice to overlap with at least one of the sleeve orifices and at least one of the body orifices to allow leak during respiratory therapy.

7. The method of claim 6, wherein one or more properties of the leak pathway include a cross-sectional area of the leak pathway.

8. The method of claim 7, wherein the cross-sectional area of the leak pathway corresponds to one or more of a positive end expiratory pressure (PEEP) or a leak flow rate.

9. The method of claim 6, wherein individual sleeve orifices have different cross-sectional areas that correspond to individual positive end expiratory pressures (PEEP).

10. The method of claim 6, wherein the adjustable leak valve further comprises one or more physical computer processors, the method further comprising determining, with the one or more physical computer processors, a cross-sectional area for the leak pathway and controlling rotation of the sleeve and the dial based on the determined cross-sectional area.

11. An adjustable leak valve configured to control leak during respiratory therapy, the valve comprising:
   means for forming a flow path, the means for forming a flow path formed along a first axis of the valve and having a first end, a second end, and a wall, the means for forming a flow path configured to conduct gas between the first end and the second end during respiratory therapy, the means for forming a flow path having body orifices formed in the wall that communicate gas from the flow path through the wall;
   means for substantially surrounding the body orifices, the means for substantially surrounding the body orifices rotatable about the first axis with respect to the means for forming a flow path, the means for substantially surrounding the body orifices having sleeve orifices formed therein, the sleeve orifices being formed in the means for substantially surrounding the body orifices and being positionable to overlap along the first axis with the body orifices; and
   means for substantially surrounding the sleeve orifices, the means for substantially surrounding the sleeve orifices having a tubular shape, the means for substantially surrounding the sleeve orifices being rotatable about the first axis with respect to the means for substantially surrounding the body orifices, the means for substantially surrounding the sleeve orifices substantially surrounding the sleeve orifices, the means for substantially surrounding the sleeve orifices having a dial orifice formed therein, the dial orifice being formed in the means for substantially surrounding the sleeve orifices and positionable to overlap with the sleeve orifices and the body orifices;

wherein, a rotational coupling between the means for forming a flow path, the means for substantially surrounding the body orifices, and the means for substantially surrounding the sleeve orifices facilitates adjustable configuration of one or more properties of a leak pathway formed by positioning the overlapping of the dial orifice with at least one of the sleeve orifices and one of the body orifices to allow leak during respiratory therapy.

12. The valve of claim 11, wherein the means for forming a flow path, the means for substantially surrounding the body orifices, and the means for substantially surrounding the sleeve orifices are configured such that the one or more properties of the leak pathway include a cross-sectional area of the leak pathway.

13. The valve of claim 12, wherein the means for forming a flow path, the means for substantially surrounding the body orifices, and the means for substantially surrounding the sleeve orifices are configured such that the cross-sectional area of the leak pathway corresponds to one or more of a positive end expiratory pressure (PEEP) or a leak flow rate.

14. The valve of claim 11, wherein the means for substantially surrounding the body orifices is configured such that individual sleeve orifices have different cross-sectional areas that correspond to individual positive end expiratory pressures (PEEP).

15. The valve of claim 11, wherein rotation of the means for substantially surrounding the body orifices, and the means for substantially surrounding the sleeve orifices is caused by one or more physical computer processors, the one or more physical computer processors configured to determine a cross-sectional area for the leak pathway and control rotation of the means for substantially surrounding the body orifices and the means for substantially surrounding the sleeve orifices based on the determined cross-sectional area.

* * * * *